United States Patent [19]

Kim et al.

[11] Patent Number: 5,462,935
[45] Date of Patent: Oct. 31, 1995

[54] CEPHALOSPORIN COMPOUNDS

[75] Inventors: Yong Z. Kim; Hun S. Oh; Jae H. Yeo; Jong C. Lim; Chan S. Bang; Won S. Kim; Hyeon J. Yim, all of Daejeon, Rep. of Korea

[73] Assignee: Lucky Limited, Yongdungpo, Rep. of Korea

[21] Appl. No.: 971,986

[22] Filed: Feb. 10, 1993

[30] Foreign Application Priority Data

Aug. 17, 1990 [KR] Rep. of Korea .................. 90-12892

[51] Int. Cl.⁶ .................. C07D 50/36; A61K 3/545
[52] U.S. Cl. .................. 514/206; 540/227
[58] Field of Search .................. 540/227; 514/206

[56] References Cited

U.S. PATENT DOCUMENTS

| | | | |
|---|---|---|---|
| 5,142,041 | 8/1992 | Kim et al. | 540/226 |
| 5,202,315 | 4/1993 | Kim et al. | 540/227 |
| 5,292,733 | 3/1994 | Kim et al. | 540/227 |

*Primary Examiner*—Nicholas Rizzo
*Attorney, Agent, or Firm*—William F. Pinsak

[57] ABSTRACT

The present invention provides a cephalosporin compound represented by formulas (I-S) and (I-R)

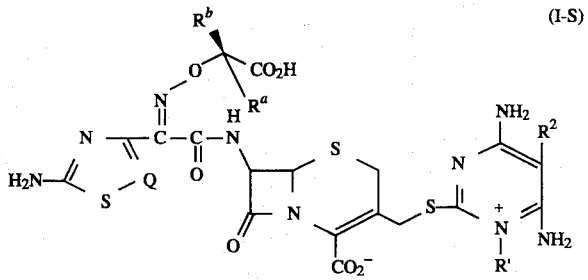

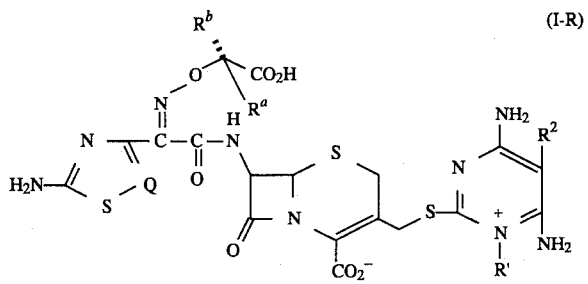

wherein:

$R^1$ is a $C_{1-4}$ alkyl, $C_{3-4}$ alkenyl, $C_{3-4}$ cycloalkyl, amino optionally substituted with a $C_{1-4}$ alkyl radical, phenyl, or 2-,4- or 6- substituted phenyl group with two or fewer substitutents chosen from $C_{1-4}$ alkyl, $C_{1-3}$ alkoxy, halogen and hydroxy radicals;

$R^2$ is hydrogen or a $C_{1-4}$ alkyl group;

$R^a$ and $R^b$, which should be different from each other, are hydrogen or a $C_{1-4}$ alkyl group; and Q is N or CH, and the pharmaceutically acceptable non-toxic salts, physiologically hydrolyzable esters, hydrates and solvates thereof, which possess potent and broad antibacterial activities. The invention also provides processes for preparing these compounds and to pharmaceutical compositions containing them as active ingredients.

11 Claims, No Drawings

CEPHALOSPORIN COMPOUNDS

FIELD OF THE INVENTION

The present invention relates to novel cephalosporin compounds, pharmaceutically acceptable non-toxic salts thereof, and physiologically hydrolyzable esters, hydrates and solvates thereof, which possess potent and broad antibacterial activities. The invention also relates to processes for preparing these compounds and to pharmaceutical compositions containing them as active ingredients.

DESCRIPTION OF THE PRIOR ART

Antibiotics of cephalosporin series are widely used in therapy for treatment of diseases which are caused by general pathogenic bacteria in human beings and animals. It has been known that such antibiotics are useful for the treatment of diseases caused by bacteria exhibiting resistance to other antibiotics, e.g., penicillin-resistant bacteria, and for treatment of penicillin-sensitive patients.

In most circumstances, it is desirable to employ antibiotics possessed with broad antibacterial activities, e.g., against both Gram-positive and Gram-negative bacteria. In this regard, there were many studies made in developing a variety of cephalosporin antibiotics with such broad-spectrum antibiotic activities.

For example, GB Patent No. 1,399,086 disclosed 7β-acylamido-ceph- 3-em-4-carboxylic acids having the formula of:

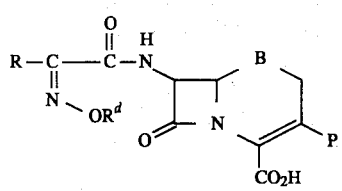

(A)

wherein:

R is hydrogen or an organic group;

$R^d$ is an etherifying monovalent organic group linked to the oxygen atom through a carbon atom;

B is S or S→O; and

P is an organic group,

Stimulated by the discovery of these compounds, there followed many attempts to develop antibiotic compounds having improved properties with respect to certain microorganisms, especially to Gram-negative bacteria. Such efforts resulted in the development of, e.g., those compounds disclosed In GB Patent No. 1,522,140, which have the following formula (B) and exist as syn isomers or as a mixture of syn and antisomers wherein the syn isomers are present in at least 90%:

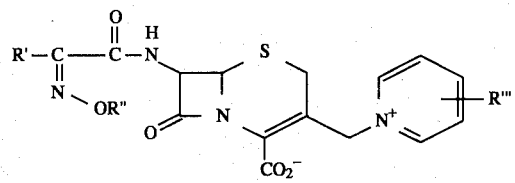

(B)

wherein:

R' is a furyl or thienyl group;

R" is a $C_{1-4}$ alkyl, $C_{3-7}$ cycloalkyl, furylmethyl or thienylmethyl group; and R'" is hydrogen or a carbamoyl, carboxy, carboxymethyl, sulfonyl or methyl group.

Recently, further efforts were made to prepare new and improved antibiotics, typically by way of introducing an acylamido group into the 7-position and certain other groups into the 3'-position of the cephem nucleus as shown in the foregoing formula (B)[see, e.g., BE Patent No. 852,427 assigned to Fujisawa; GB Patent Nos. 1,603,212 and 1,604,971, both assigned to Hoechst A.G.; EP Application No. 47,977 assigned to Ciba-Geigy; EP Application No. 74,563 assigned to Bayer; and U.S. Pat. No. 4,390,534 and EP Application No. 62,321, both assigned to Fujisawal. Among these prior art references, of particular interest are U.S. Pat. Nos. 4,258,041 and 4,329,453, both assigned to Glaxo.

In particular, the cephalosporin compound singularly claimed in the latter patent, i.e., U.S. Pat. No, 4,329,453, commonly known as "Ceftazidime", is one of the commercially successful and potent cephem derivatives having a broad spectrum of antibiotic activities against various organisms normally difficult to combat with β-lactam antibiotics, said Ceftazidime can be represented by the following formula:

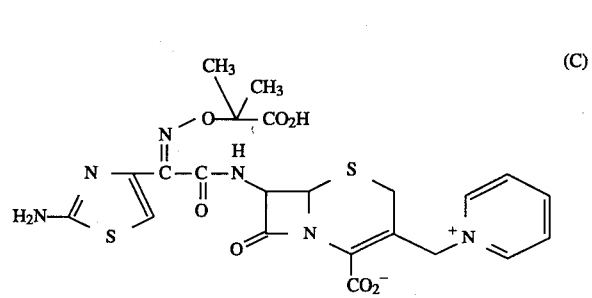

(C)

As disclosed in European. Patent Application No. 397, 511, the inventors of the present invention have also discovered that those novel antibiotic cephalosporin compounds having the following structural formula (D), their pharmaceutically acceptable non-toxic salts, physiologically hydrolyzable esters and solvates have surprisingly superior antibiotic activity against a wide range of organisms:

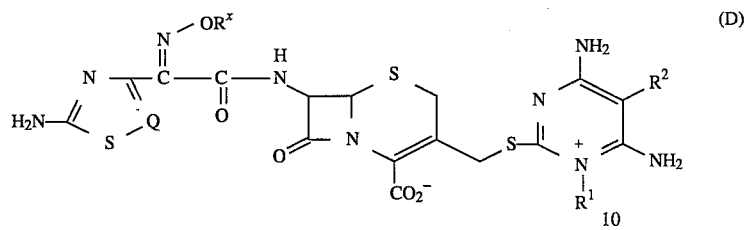

(D)

wherein:
$R^x$ is a $C_{1-4}$ alkyl, $C_{3-4}$ alkenyl, $C_{3-4}$ alkynyl group, or —$C(R^a)(R^b)CO_2H$, wherein $R^a$ and $R^b$, which may be same or different, are hydrogen or a $C_{1-4}$ alkyl group or $R^a$ and $R^b$ form a $C_{3-7}$ cycloalkyl group with the carbon atom to which they are linked; $R^1$ is a $C_{1-4}$ alkyl, $C_{3-4}$ alkenyl, $C_{3-7}$ cycloalkyl, amino optionally substituted with a $C_{1-4}$ alkyl radical, phenyl, or 2-, 4- or 6-substituted phenyl group with two or fewer substitutents chosen from $C_{1-4}$ alkyl, $C_{1-3}$ alkoxy, halogen and hydroxy radicals;

$R^2$ is hydrogen or a $C_{1-4}$ alkyl group; and

Q is N or CH.

The cephalosporin compounds of formula (D) are either syn isomers or mixtures of syn and anti isomers which contain at least of the syn isomer. Further, when the $R^x$ group in the formula (D) compounds is —$C(R^1)(R^b)CO_2H$, wherein $R^a$ and $R^b$ are different, the carbon atom to which $R^a$ and $R^b$ are linked becomes a chiral center and these compounds become diastereoisomers.

SUMMARY OF THE INVENTION

Unexpectedly, the present inventors have further discovered that the R and S diastereoisomers of formula (D), wherein $R^x$ is —$C(R^a)(R^b)$—$CO_2H$ and $R^a$ and $R^b$ are different so that the carbon to which they are linked becomes a chiral center, when they are isolated, particularly the S isomers, exhibit superior antibacterial activities.

Accordingly, the primary objective of the present invention is to provide novel cephalosporins of formulas (I-S) and (I-R) and pharmaceutically acceptable non-toxic salts thereof, and physiologically hydrolyzable esters, hydrates and solvates thereof.

Specifically, the S isomers of the present invention may be represented as:

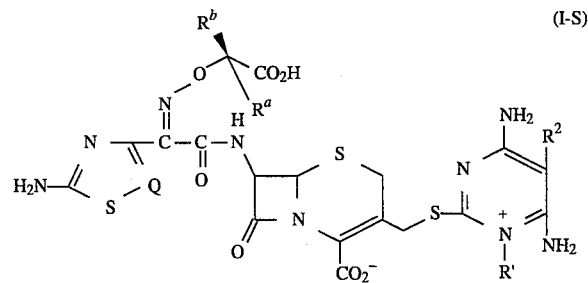

(I-S)

and the R isomers may be represented as:

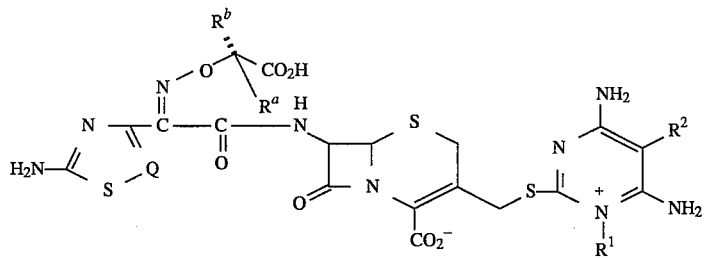

(I-R)

wherein:
$R^1$ is a $C_{1-4}$ alkyl, C3-4 alkenyl, $C_{3-4}$ cycloalkyl, amino optionally substituted with a $C_{1-4}$ alkyl radical, phenyl, or 2-, 4- or 6-substituted phenyl group with two or fewer substituents chosen from $C_{1-4}$ alkyl, $C_{1-3}$ alkoxy, halogen and hydroxy radicals;

$R^2$ is hydrogen or a $C_{1-4}$ alkyl group;

$R^a$ and $R^b$, which should be different from each other, are hydrogen or a $C_{1-4}$ alkyl group; and Q is N or CH.

More preferred cephalosporin compounds of the present invention are the S isomers of formula (I-S), wherein $R^2$ is a $C_{1-4}$ alkyl, $C_{3-4}$ alkenyl or amino group; $R^2$ is hydrogen or a $C_{1-2}$ alkyl group; $R^a$ and $R^b$, which should be different from each other, are hydrogen or a $C_{1-2}$ alkyl group; and Q is CH, Most preferred cephalosporin compounds of the present invention are the S isomers of formula (I-S), wherein $R^1$ is methyl, ethyl or amino; $R^2$ is hydrogen or methyl; $R^a$ and $R^b$, which should be different from each other, are hydrogen or methyl; and Q is CH.

Another aspect of the present invention involves processes for preparing the respective isomer compounds of formulas (I-S) and (I-R), which formulas may be collectively referred to as formula (I) hereinafter.

A further feature of the present invention relates to the pharmaceutically acceptable non-toxic salts, physiologically hydrolyzable esters, hydrates and solvates of the diastereomers of formula (I) and processes for preparing these compounds, A still further novel contribution of the present invention resides in the formulation of pharmaceutical compositions comprising one or more of the cephalosporin compounds represented by formula (I) and their pharmaceutically acceptable derivatives.

DETAILED DESCRIPTION OF THE INVENTION

The novel cephalosporin compounds of formula (I) are either syn isomers or mixtures of syn and anti isomers, with respect to the radical, —O—C($R^a$)($R^b$)—$CO_2H$, which contain at least 90% of the syn isomer or not more than 10% of the anti isomer.

In addition, the compounds of formula (I) according to the present invention may exist in tautomeric forms and such tautomers are also included within the scope of the invention. Namely, when Q of formula (I) is CH, the aminothiazolyl group undergoes tautomerism to form an iminothiazolinyl group, its tautomer, as follows:

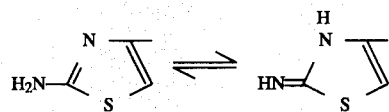

When Q of formula (I) is a nitrogen atom, the aminothiadiazolyl group forms iminothiadiazolinyl group, its tautomers, as follows:

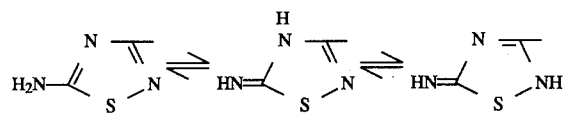

The compounds of formula (I) also include the resonance isomers. Therefore, for instance, If the compounds represented by formula (I-S), the compounds in accordance with the present invention include the following structures of formulas (I-S)' and (I-S)":

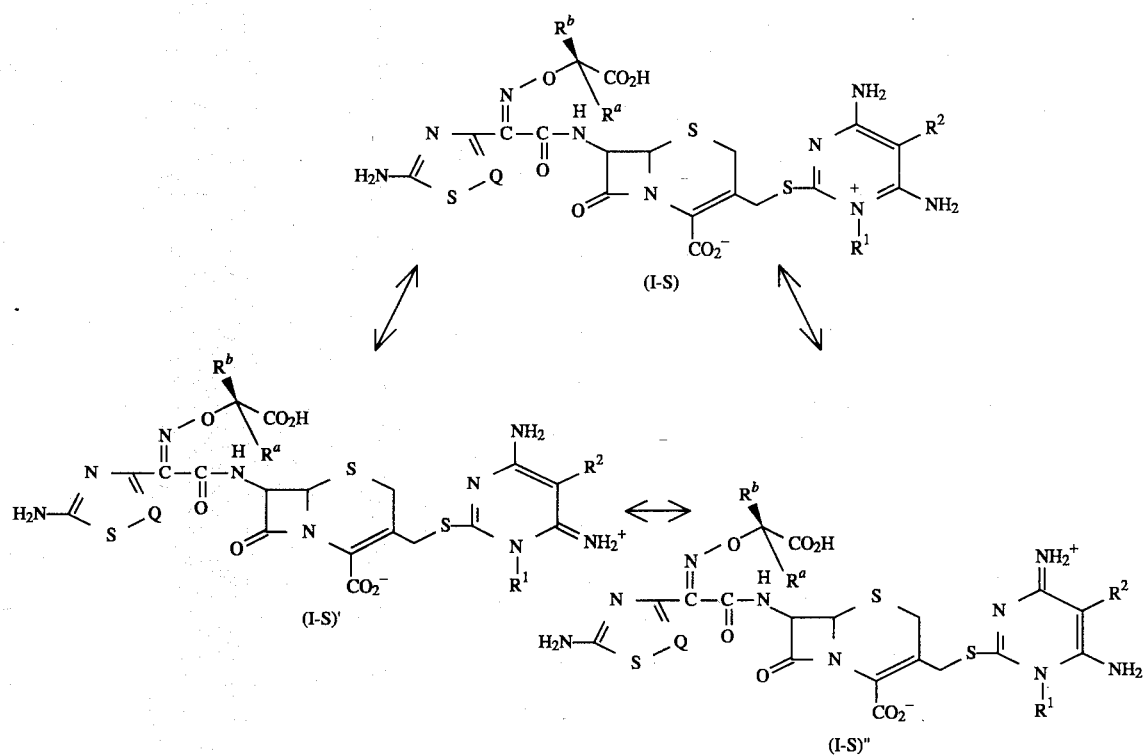

Similarly, the compounds of formula (I-R) should be taken to include their resonance isomers.

Furthermore, the present invention encompasses, within its scope, those pharmaceutically acceptable non-toxic salts, physiologically hydrolyzable esters, solvates and hydrates of the diastereomers collectively represented by formula (I). Suitable pharmaceutically acceptable salts of the cephalosporin compounds (I) are conventional non-toxic salts and may include inorganic salts, for example, metal salts such as alkali metal salts (e.g., sodium salt, potassium salt, etc.), and alkaline earth metal salts (e.g., calcium salt, magnesium salt, etc.), ammonium salt, etc.; organic salts, for example, an organic amine salt (e.g., trimethylamine salt, N-methylglucamine salt, diethanolamine salt, triethanolamine salt, triethylamine salt, pyridine salt, procaine salt, picoline salt, dicyclohexylamine salt, N,N'-dibenzylethylenediamine salt, tris(hydroxymethylamino)methane salt, phenylethylbenzylamine salt, dibenzylethylenediamine salt, etc.); organic carboxylic or sulfonic acid salts (e.g., formate, acetate, maleate, tartrate, methanesulfonate, benzenesulfonate, toluenesulfonate, etc.); inorganic acid salts (e.g., hydrochloride, hydrobromide, sulfate, phosphate, etc.); salts with basic or acidic amino acids (e.g., arginine, aspartic acid, glutamic acid, lysine, etc.); more preferably, alkali metal salts, alkaline earth metal salts, inorganic acid salts, organic carboxylic acid salts and salts with basic or acidic amino acids; and most preferably, sodium salt, potassium salt, hydrochloride and sulfate.

Above pharmaceutically acceptable non-toxic salts may be prepared by reacting the compounds of the formula (I) with one to four equivalents of corresponding acids or bases to the salts mentioned above in the presence of a solvent which may be water, or a mixture of water and water-miscible solvent (e.g.,methanol, ethanol, acetonitrile, acetone, etc).

The physiologically hydrolyzable esters of the compounds (I) may include, for example, methoxycarbonyloxymethyl, 1-methoxycarbonyloxy- 1-ethyl, indanyl, phthalidyl methoxymethyl, pivaloyloxymethyl, glycyloxymethyl, phenylglycyloxymethyl or 5-methyl-2-oxo- 1, 3-dioxolan-4-yl esters, and other physiologically hydrolyzable esters which have been widely used in the technical fields of penicillin and cephalosporin antibiotics; more preferably, methoxycarbonyloxymethyl, 1-methoxycarbonyloxy-1-ethyl, methoxymethyl or pivaloyloxymethyl; and most preferably, methoxycarbonyloxymethyl or methoxymethyl.

These esters can be prepared in accordance with known methods, e.g., by reacting the compounds of formula (I) with corresponding alkyl halides (e.g., methoxymethyl chloride or methoxycarbonyloxymethyl chloride) in the presence of a base (e.g.,triethylamine, pyridine or sodium bicarbonate).

Exemplary solvates of the cephalosporin compounds of formula (I) may include solvates with water-miscible solvents, e.g., methanol, ethanol, acetone or acetonitrile; and more preferably, ethanol.

The present invention also includes within its scope pharmaceutical compositions comprising one or more of the compounds (I) as active ingredients, in association with pharmaceutically acceptable carriers, excipients or other additives.

The antibiotic compounds (I) of the invention may be formulated for administration in unit dose or multi-dose containers. The compositions may take various forms such as solution, suspension or emulsion in an oily or aqueous vehicle, which can contain conventional additives such as a dispersant, suspending agent, stabilizer and the like. Alternatively, the active ingredient may be formed into a dried powder that can be normally dissolved in an aqueous solution of sterile pyrogen-free water before use. The compounds (I) may be also formulated into suppositories containing conventional suppository bases such as cocoa butter or other glycerides.

The pharmaceutical compositions in a unit dose form may preferably comprise about from 50 to 1,500mg of the active ingredient, depending on the age and body weight of the patient, the nature and severity of the illness, and so on. In general, it has been shown advantageous to administer the active compounds in an amount of about 500 to 5,000mg per day in order to achieve the desired results, depending on the routes and frequency of administration. In case of intramuscular or intravenous administration for adult human treatment, the dosage of about 150 to 3,000 mg per day is thought to be sufficient, although it may vary in case of treatment for specific infections caused by certain strains.

If desired, the compounds (I) can be administered in combination with other antibiotics such as penicillins or other cephalosporins.

The compounds of the present invention, as described above, exhibit potent and broad antibacterial activities against Gram-positive bacteria and a variety of Gram-negative bacteria as well, particularly against Pseudomonas. Also, these compounds have high stability to β-lactamases produced by a number of Gram-negative bacteria.

The diastereomers of formula (I) may be produced by a number of different methods. One of them is to simply isolate the S and R isomers by chromatography, with an eluent, from a mixture of the isomers.

Exemplary eluents which may be employed in the separation process include: a mixture of buffer and water-miscible solvent (e.g., methanol, acetonitrile, isopropyl alcohol); and more preferably, a mixture of buffer and acetonitrile.

Said isolation process may be conducted under the following conditions:

Eluent: Buffer/CH$_3$CN=85/15~95/5(v/v)
  (Buffer: phosphate, pH 7.0, 0.01M)

Column: ODS Column

Detector: UV 254 nm

The preferred method of preparing a compound of formula (I) comprises reacting a compound of formula (II-S) or (II-R), which may be collectively referred to as formula (II) hereinafter, in the presence of a solvent, with a compound of formula (III) as follows:

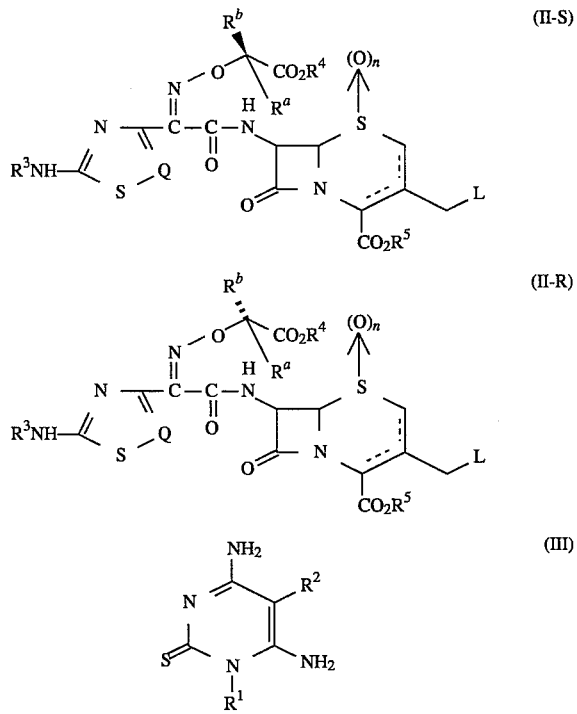

wherein:

$R^a$, $R^b$, $R^1$, $R^2$ and Q have the same meanings as defined above;

n is 0 or 1;

$R^3$ is hydrogen or an amino protecting group;

$R^4$ is hydrogen or a carboxyl protecting group;

$R^5$ is hydrogen or a carboxyl protecting group; and

L is a leaving group.

The amino protecting group in $R^3$ above may include acyl substituted or unsubstituted aryl(lower)alkyl (e.g., benzyl, diphenylmethyl, triphenylmethyl and 4-methoxybenzyl), halo(lower) alkyl (e.g., trichloromethyl and trichloroethyl), tetrahydropyranyl, substituted phenylthio, substituted alkylidene, substituted aralkylidene or substituted cycloalkylidene. The acyl group as an amino protecting group may include, for example, $C_{1-6}$(lower) alkanoyl (e.g., formyl and acetyl), $C_{2-6}$ alkoxycarbonyl (e.g., methoxycarbonyl and ethoxycarbonyl), (lower)alkanesulfonyl (e.g., methanesulfonyl and ethanesulfonyl), or aryl (lower)alkoxycarbonyl (e.g., benzyloxycarbonyl), where the acyl group can be substituted with 1–3 substituent(s) such as halogen, hydroxy, cyano or nitro. In addition, the amino protecting group may include reaction products obtained from amino groups and silane, boron or phosphorus compounds.

The carboxyl protecting group of $R^4$ or $R^5$ may include, for example, (lower)alkylesters (e.g., methylester and t-butylester), (lower)alkenylesters (e.g., vinylester and allylester), (lower) alkoxy(lower)alkylesters(e.g., methoxymethylester), (lower)alkylthio(lower)alkylesters (e.g., methylthiomethylester), halo(lower) alkylesters (e.g., 2,2,2-trichloroethylester), substituted or unsubstituted aralkylesters (e.g., benzylester and p-nitrobenzylester) or silylesters, which can be selected after consideration of the chemical property of the desired compounds (I).

The leaving group L in formula (III) may include, for example, halogen such as chlorine or bromine, a (lower)alkanoyloxy group such as acetoxy, a (lower)alkanesulfonyloxy group such as methanesulfonyloxy, an arenesulfonyloxy group such as p-toluenesulfonyloxy, an alkoxycarbonyloxy group and the like.

The term "lower" as used hereinabove and elsewhere in this specification, for example in reference to "lower alkyl," encompasses groups having 1 to 6 carbon atoms, more preferably, 1 to 4 carbon atoms.

In the preparation of the objective compounds (I), the compounds of the formula (II) are used preferably in an amount of from 1 to 2 molar equivalents based on the compounds of the formula (III).

Amino or acid protecting groups can be readily removed by any of the conventional deprotection methods which are well known in the field of cephalosporin antibiotics. For example, acid- or base-hydrolysis or reduction is generally applicable. For further example, when the protecting group is an amido group, It is feasible to subject such compounds to imino-halogenation and iminoetherification, and then followed by hydrolysis. Acid hydrolysis is preferred to remove such groups as tri(di)phenylmethyl or alkoxycarbonyl; and is carried out in the presence of an organic acid, such as formic acid, trifluoroacetic acid, or p-tolueneacetic acid, or an inorganic acid such as hydrochloric acid and the like.

Reduction of S-oxide can be conventionally carried out, for example, by adding potassium iodide and acetyl chloride to the reactants, followed by quenching the reaction mixture with sodium m-bisulfite.

The reaction for introducing the compounds (III) into the 3-position of the compounds (II) to prepare the compounds (I) is carried out in the presence of a solvent such as water, or a mixture of water and a water-miscible solvent, wherein the pH of the reaction solution may range from 5 to 8, more preferably, from 6 to 7.5; and the temperature may range from 20° to 100° C., more preferably from 60° to 80° C.

The starting materials of the compounds (II) are known intermediates conventionally employed for the preparation of cephalosporin compounds. The dotted line of formula (II) represents a single bond or a double bond; and, therefore, the compounds of formula (II) may be the compounds of formula (II-a), or the compounds of formula (II-b), or mixtures thereof:

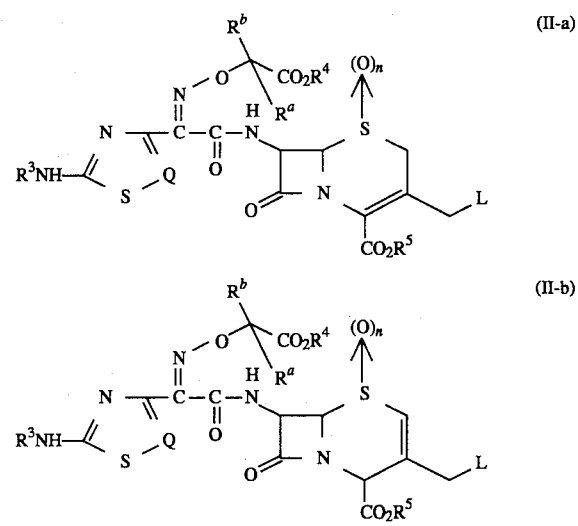

wherein
n, $R^a$, $R^b$, $R^3$, $R^4$, $R^5$, Q and L have the same meanings as defined before.

To stabilize the reaction products and their intermediates, one or more salts selected from the group consisting of sodium iodide, potassium iodide, sodium bromide, potassium bromide and potassium thiocyanate can be used as a stabilizer.

The separation and purification of the compounds (I) can be carried out using a conventional method such as recrystallization, column chromatography over silica gel or ion-exchange chromatography.

The following examples illustrate how some of the compounds of formula (I) can be prepared.

EXAMPLE 1

Synthesis of Compound (I-S-1)

This example shows how one of the preferred compounds, 7-[(Z)-2-(2-aminothiazol-4-yl)-2-[(S)-1-carboxy-eth-1-oxyimino] acetamido]-3-[(1,4,6-triaminopyrimidinium-2-yl)thiomethyl]-3-cephem- 4-carboxylate, having the following formula, was synthesized:

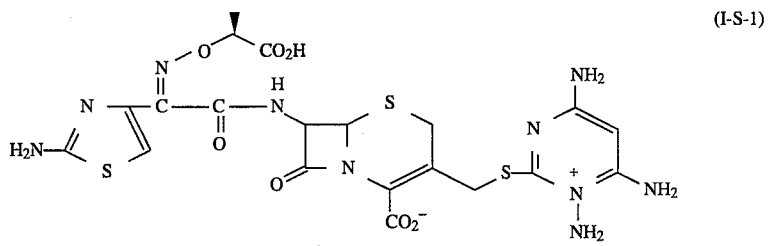

(I-S-1)

To a solution containing 500 mg of 3-acetoxymethyl-7-[(Z)- 2-(2-aminothiazol-4-yl)-2-[(S)-1-carboxyeth-1-oxyimino]acetamido]- 3-cephem-4-carboxylic hydrochloride suspended in 5 ml of distilled water were added 200 mg of 1,4,6-triamino-2(1H)-pyrimidinethione and 800 mg of potassium iodide. The reaction solution was heated to 70° C., while the pH was adjusted to 7.1 to 7.2 with addition of aqueous sodium bicarbonate solution. The resultant solution was stirred for 4 hours, cooled to room temperature and adjusted to pH 3 to 3.5 with 2N-aqueous hydrochloric acid solution to produce precipitates which were washed with 5ml of distilled water after filtration. The filter cake was applied to the chromatography on prep-column (ODS steel column, 19 mm×300 mm) using mixtures of ammonium phosphate buffer solution at pH 7 and acetonitrile (95:5) as an eluent, to give 190 mg of the title compound as a white solid (m.p.>195° C., dec.).

NMR: δ ($D_2O$, $NaHCO_3$, 270 MHz) 1.46(d, 3H), 3.58(ABq, 2H), 4.22(ABq, 2H), 4,65(q, 1H), 5.17(d, 1H), 5.56(s, 1H), 5.79(d, 1H), 7.00(s, 1H).

MS: 611(FAB, M+1)

IR(KBr, $cm^{-1}$): 1771(β-lactam), 1650, 1535

UVλ$max^{HO}$ (nm,ε): (220, 33957), (232, 34794), (275, 23323), (274, 23915)

[α]$_D^{25}$: −105.5° (C 1.0, 0.05N aqueous sodium bicarbonate solution)

HPLC analysis condition
column: μ-Bondapak C-18
detector: UV 254 nm
flow rate: 2 ml/min
retention time: 7.2 min

EXAMPLE 2

Synthesis of Compound (I-S-2)

This example shows how one of the preferred compounds, 7-[(Z)-2-(2-aminothiazol-4-yl)-2-[(S)-1-carboxyeth-1-oxyimino]acetamido] -3-[(4,6-diamino-1-methylpyrimidinium-2-yl)thiomethyl]-3-cephem- 4-carboxylate, having the following formula (I-S-2), was synthesized:

To a solution containing 500 mg of 3-acetoxymethyl-7-[(Z)-2-(2-aminothiazol-4-yl)-2-[(S)-1-carboxyeth-1-oxyimino]acetamido] -3-cephem-4-carboxylic hydrochloride suspended in 5 ml of distilled water were added 200 mg of 4,6-diamino-1-methyl-2-(1H)-pyrimidinethione and 800 mg of potassium iodide. The reaction solution was heated to 70° C., while the pH was adjusted to 7.1 to 7.2 with addition of aqueous sodium bicarbonate solution. The resultant solution was stirred for 4 hours, cooled to room temperature and adjusted to pH 3 to 3.5 with 2N-aqueous hydrochloric acid solution to produce precipitates which were washed with 5 ml of distilled water after filtration. The filter cake was applied to the chromatography on prep-column (ODS steel column, 19 mm×300 mm) using mixtures of ammonium phosphate buffer solution at pH 7 and acetonitrile (92:8) as an eluent, to give 195 mg of the title compound as a white solid (m.p.>180° C., dec.).

NMR: δ ($D_2O$, $NaHCO_3$, 270(MHz) 1.49(d, 3H), 3.59(s, 3H), 3.59(ABq, 2H), 4.36 (ABq, 2H), 4.67(q, 1H), 5.17(d, 1H), 5.61(s, 1H), 5.79(d, 1H), 7.01(s, 1H).

MS: 610(FAB, M+1)

IR(KBr, $cm^{-1}$): 1775(β-lactam), 1635, 1535

UVλ$max^{HO}$ (nm,ε): (217, 34252), (232, 32672), (275, 23323)

[α]$_D^{25}$: −124.1° (C 1.0, 0.05N aqueous sodium bicarbonate solution)

EXAMPLE 3

Synthesis of compound (I-S-3)

This example shows how one of the preferred compounds, 7[(Z)-2-(2-aminothiazol-4-yl)-2[(S)-1-carboxyeth-1-oxyimino] acetamido]-3-[(4,6-diamino-1-ethylpyrimidinium-2-yl)thiomethyl]- 3-cephem-4-carboxylate, having the following formula (I-S-3), was synthesized:

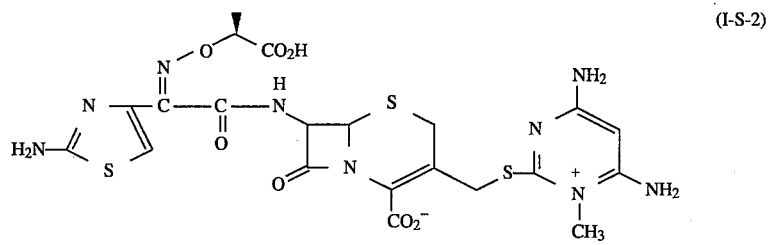

(I-S-2)

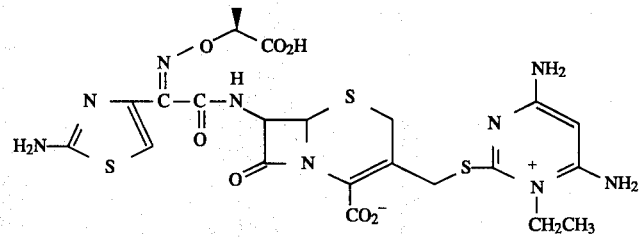

(I-S-3)

To a solution containing 500 mg of 3-acetoxymethyl-7-[(Z)- 2-(2-aminothiazol-4-yl)-2-[(S)-1-carboxyeth-1-oxyimino]acetamido]- 3-cephem-4-carboxylic hydrochloride suspended in 5ml of distilled water were added 200 mg of 4,6-diamino-1-ethyl-2(1H)-pyrimidinethione and 800 mg of potassium iodide. The reaction solution was heated to 70° C., while the pH was adjusted to 7.1 to 7.2 with addition of aqueous sodium bicarbonate solution. The resultant solution was stirred for 4 hours, cooled to room temperature and adjusted to pH 3 to 3.5 with 2N-aqueous hydrochloric acid solution to produce precipitates which were washed with 5 ml of distilled water after filtration. The filter cake was applied to the chromatography on prep-column (ODS steel column, 19 mm×300 mm) using mixtures of ammonium phosphate buffer solution at pH 7 and acetonitrile (92:8) as an eluent, to give 180 mg of the title compound as a white solid (m.p.>193° C. dec.).

NMR: $\delta(D_2O, NaHCO_3, 270$ MHz) 1.34(t, 3H), 1.48(d, 3H), 3.59(ABq, 2H), 4.04(q, 2H), 4.34(ABq, 2H), 4.67(d, 1H), 5.15(d, 1H), 5.58(s, 1H), 5.79(d, 1H), 7.01(s, 1H).

MS: 624(FAB, M+1)

IR(KBr, $cm^{-1}$): 1775(β-lactam), 1640, 1530.

UVλmax$^{HO}$(nm,ε): (220, 34648), (234, 32700), (276, 22620)

$[\alpha]_D^{25}$: −110.3° (C 1.0, 0.05N aqueous sodium bicarbonate solution)

EXAMPLE 4

Synthesis of Compound (I-S-4)

This example shows how one of the preferred compounds, 7-[(Z)-2-(2-aminothiazol-4-yl)-2-[(S)-1-carboxyeth-1-oxyimino]acetamido] -3-[(4,6-diamino-1-propylpyrimidinium-2-yl)thiomethyl]-3-cephem- 4-carboxylate, having the following formula (I-S-4), was synthesized:

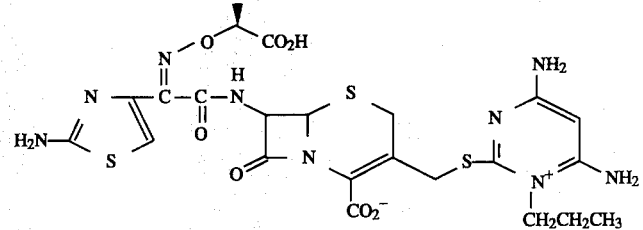

(I-S-4)

To a solution containing 500 mg of 3-acetoxymethyl-7-[(Z)- 2-(2-aminothiazol-4-yl)-2-[(S)-1-carboxyeth-1-oxyimino]acetamido]-3-cephem-4-carboxylic hydrochloride suspended in 5 ml of distilled water were added 200 mg of 4,6-diamino-1-propyl-2(1H)-pyrimidinethione and 800 mg of potassium iodide. The reaction solution was heated to 70° C., while the pH was adjusted to 7.1 to 7.2 with addition of aqueous sodium bicarbonate solution. The resultant solution was stirred for 4 hours, cooled to room temperature and adjusted to pH 3 to 3.5 with 2N-aqueous hydrochloric acid solution to produce precipitates which were washed with 5 ml of distilled water after filtration. The filter cake was applied to the chromatography on prep-column (ODS steel column 19 mm×300 mm) using mixtures of ammonium phosphate buffer solution at pH 7 and acetonitrile (90:10) as an eluent, to give 150 mg of the title compound as a white solid (m.p.>197° C., dec.).

NMR: $\delta(D_2O, NaHCO_3, 270$ MHz) 0.98(t, 3H), 1.48(d, 3H), 1.77(m, 2H), 3.61(ABq, 2H), 3.97(t, 2H), 4.38(ABq, 2H), 4.68(q, 1H), 5.19(d, 1H), 5.60(d, 1H), 5.81(d, 1H), 7.01(s, 1H).

MS: 638(FAB, M+1)

IR(KBr, $cm^{-1}$): 1778(β-lactam), 1645, 1525

UVλmax$^{HO}$(nm,ε): (222, 37377), (232, 35410), (276, 23831).

$[\alpha]D^{25}$: −105.4° (C 1.0, 0.05N aqueous sodium bicarbonate solution)

EXAMPLE 5

Synthesis of Compound (I-S-5)

This example shows how one of the preferred compounds, 7-[(Z)-2-(2-aminothiazol-4-yl)-2-[(S)-1-carboxyeth-1-oxyimino] acetamido]-3-[(4,6-diamino-1-phenylpyrimidinium-2-yl)thiomethyl]- 3-cephem-4-carboxylate, having the following formula (I-S-5), was synthesized:

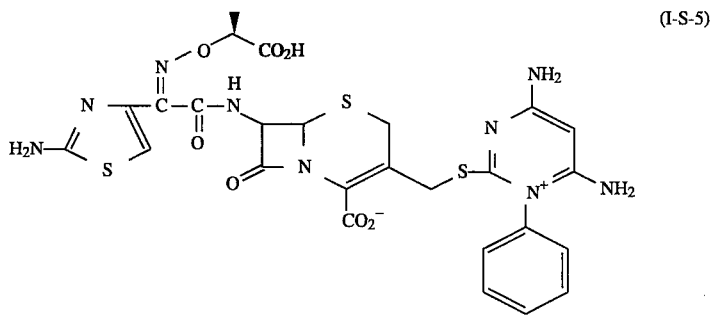
(I-S-5)

To a solution containing 500 mg of 3-acetoxymethyl-7-[(Z)- 2-(2-aminothiazol-4-yl)-2-[(S)-1-carboxyeth-1-oxyimino]acetamido]-3-cephem-4-carboxylic hydrochloride .suspended in 5 ml of distilled water were added 200 mg of 4,6-diamino-1-phenyl-2(1H)-pyrimidinethione and 800 mg of potassium iodide. The reaction solution was heated to 70°, while the pH was adjusted to 7.1 to 7.2 with addition of aqueous sodium bicarbonate solution. The resultant solution was stirred for 4 hours, cooled to room temperature and adjusted to pH to 3.5 with 2N-aqueous hydrochloric acid solution to produce precipitates which were washed with 5 ml of distilled water after filtration. The filter cake was applied to the chromatography on prep-column (ODS steel column 19 mm×300 mm) using mixtures of ammonium phosphate buffer solution at pH 7 and acetonitrile(87:13) as an eluent, to give 120 mg of the title compound as a white solid (m.p.>190° C., dec.).

NMR: $\delta(D_2O,\ NaHCO_3,\ 270\ MHz)$ 1.48(d, 3H), 3.48(ABq, 2H), 4.25(ABq, 2H), 4.67(q, 1H), 5.14(d, 1H), 5.69(s, 1H), 5.79(d, 1H), 7.00(s, 1H), 7.43–7.81(m, 5H).

MS: 672(FAB, M+1)

IR(KBr, $cm^{-1}$): 1777($\beta$-lactam), 1650, 1515

UV$\lambda max^{HO}$(nm,$\epsilon$): (221, 31548), (235, 29524), (273, 18827).

$[\alpha]_D^{25}$ –8.1° (C 1.0, 0.05N aqueous sodium bicarbonate solution)

EXAMPLE 6

Synthesis of Compound (I-S-6)

This example shows how one of the preferred compounds, 7-[(Z)-2-(2-aminothiazol-4-yl)-2-[(S)-1-carboxyeth-1-oxyimino] acetamido]-3-[(4,6-diamino-1,5-dimethylpyrimidinium-2-yl)thiomethyl]- 3-cephem-4-carboxylate, having the following formula (I-S-6), was synthesized:

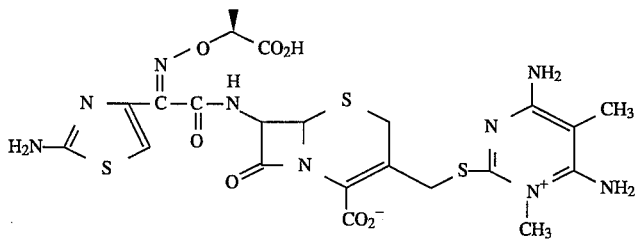
(I-S-6)

To a solution containing 500 mg of 3-acetoxymethyl-7-[(Z)- 2-(2-aminothiazol-4-yl)-2-[(S)-1-carboxyeth-1-oxyimino]acetamido]- 3-cephem-4-carboxylic hydrochloride suspended in 5 ml of distilled water were added 200 mg of 4,6-diamino-1,5-dimethyl-2(1H)-pyrimidinethione and 800 mg of potassium iodide. The reaction solution was heated to 70° C., while the pH was adjusted to 7.1 to 7.2 with addition of aqueous sodium bicarbonate solution. The resultant solution was stirred for 4 hours, cooled to room temperature and adjusted to pH 3 to 3.5 with 2N-aqueous hydrochloric acid solution to produce precipitates which were washed with 5 ml of distilled water after filtration. The filter cake was applied to the chromatography on prep-column (ODS steel column 19 mm×300 mm) using mixtures of ammonium phosphate buffer solution at pH 7 and acetonitrile (91:9) as an eluent, to give 210 mg of the title compound as a white solid (m.p.>183° C., dec. ).

NMR: $\delta(D_2O,\ NaHCO_3,\ 270\ MHz)$ 1.48(d, 3H), 1.92(s, 3H), 3.57(s, 3H), 3.60(ABq, 2H), 4.38(ABq, 2H), 4.69(q, 1H), 5.17(d, 1H), 5.81(s, 1H), 7.03(s, 1H).

MS:. 672(FAB, M+1)

IR(KBr, $cm^{-1}$): 1765($\beta$-lactam), 1645, 1560

UV$\lambda max^{HO}$(nm,$\epsilon$): (203, 34313), (232, 32588), (281, 24089).

$[\alpha]_D^{25}$: –121.4° (C 1.0, 0.05N aqueous sodium bicarbonate solution)

EXAMPLE 7

Synthesis of Compound (I-S-7)

This example shows how one of the preferred compounds, 7-[(Z)-2-(2-aminothiazol-4-yl)-2-[(S)-1-carboxyeth-1-oxyimino] acetamido]-3-[(5-methyl-1,4,6-triaminopyrimidinium-2-yl)thiomethyl]- 3-cephem-4-carboxylate, having the following formula (I-S-7), was synthesized:

(I-S-7)

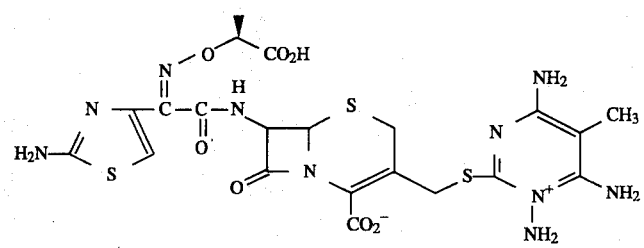

To a solution containing 500 mg of 3-acetoxymethyl-7-[(Z)- 2-(2-aminothiazol-4-yl)-2-[(S)-1-carboxyeth-1-oxyimino]acetamido]-3-cephem-4-carboxylic hydrochloride suspended in 5 ml of distilled water were added 200 mg of 5-methyl-1,4,6-triamino-2(1H)-pyrimidinethione and 800 mg of potassium iodide. The reaction solution was heated to 70° C., while the pH was adjusted to 7.1 to 7.2 with addition of aqueous sodium bicarbonate solution, The resultant solution was stirred for 4 hours, cooled to room temperature and adjusted to pH 3 to 3.5 with 2N-aqueous hydrochloric acid solution to produce precipitates which were washed with 5 ml of distilled water after filtration. The filter cake was applied to the chromatography on prep-column (ODS steel column, 19 mm×300 mm) using mixtures of ammonium phosphate buffer solution at pH 7 and acetonitrile (93:7) as an eluent, to give 220 mg of the title compound as a white solid (m.p.>181° C., dec.).

NMR: $\delta(D_2O$, $NaHCO_3$, 270MHz) 1.48(d, 3H), 1.85(s, 3H), 3.58(ABq, 2H), 4.32(ABq, 2H), 4.67(q, 1H), 5.18(d, 1H), 5.77(d, 1H), 6.94(s, 1H).

MS: 625(FAB, M+1)

IR(KBr, $cm^{-1}$): 1770(β-lactam). 1635, 1565

UVλ$max^{HO}$(nm,ε): (204, 35861), (232, 35288), (281, 24807).

$[\alpha]_D^{25}$: −118.0° (C 1.0, 0.05N aqueous sodium bicarbonate solution)

EXAMPLE 8

Synthesis of Compound (I-R-1)

This example shows how one of the isomeric compounds, 7-[(Z)-2-(2-aminothiazol-4-yl)-2-[(R)-1-carboxyeth-1-oxyimino] acetamido]-3-[(1,4,6-triaminopyrimidinium-2-yl)thiomethyl]-3-cephem- 4-carboxylate, having the following formula (I-R-1), was synthesized:

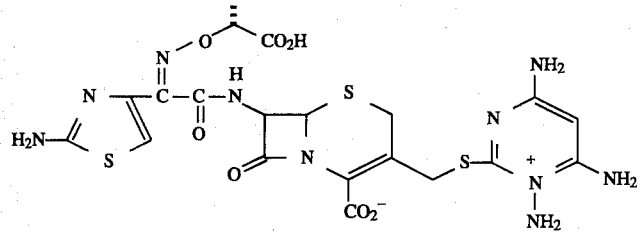

(I-R-1)

To a solution containing 500 mg of 3-acetoxymethyl-7-[(Z)- 2-(2-aminothiazol-4-yl)-2-[(R)-1-carboxyeth-1-oxyimino]acetamido]- 3-cephem-4-carboxylic hydrochloride suspended in 5 ml of distilled water were added 200 mg of 1,4,6-triamino-2(1H)-pyrimidinethione and mg of potassium iodide. The reaction solution was heated to 70° C., while the pH was adjusted to 7.1 to 7.2 with addition of aqueous sodium bicarbonate solution. The resultant solution was stirred for 4 hours, cooled to room temperature and adjusted to pH to 3.5 with 2N-aqueous hydrochloric acid solution to produce precipitates which were washed with 5 ml of distilled water after filtration. The filter cake was applied to the chromatography on prep-column (ODS steel column, 19 mm×300 mm) using mixtures of ammonium phosphate buffer solution at pH 7 and acetonitrile (95:5) as an eluent, to give 180 mg of the title compound as a white sol 1d (m.p.>190° C., dec. ).

NMR: $\delta(D_2O$, $NaHCO_3$, 270 MHz) 1.46(d, 3H), 3.58(ABq, 2H), 4.22(ABq, 2H), 4.65(q, 1H), 5.17(d, 1H), 5.56(s, 1H), 5.71(d, 1H), 7.00(s, 1H).

MS: 611(FAB, M+1)

IR(KBr, $cm^{-1}$): 1772(β-lactam), 1650, 1530

UVλ$max^{HO}$(nm,ε): (218, 32713), (232, 31842), (275, 21786).

$[\alpha]_D^{25}$: −48.7° (C 1.0, 0.05N aqueous sodium bicarbonate solution)

HPLC analysis condition column: μ-Bondapak C-18 detector: UV 254 nm flow rate: 2 ml/min retention time: 11.5 min

EXAMPLE 9

Synthesis of Compound (I-R-2)

This example shows how one of the isomeric compounds, 7-[(Z)-2-(2-aminothiazol-4-yl)-2-[(R)-1-carboxyeth-1-oxyimino] acetamido]-3-[(4,6-diamino-1-methylpyrimidinium-2-yl)thiomethyl]-3-cephem-4-carboxylate, having the following formula (I-R-2), was synthesized:

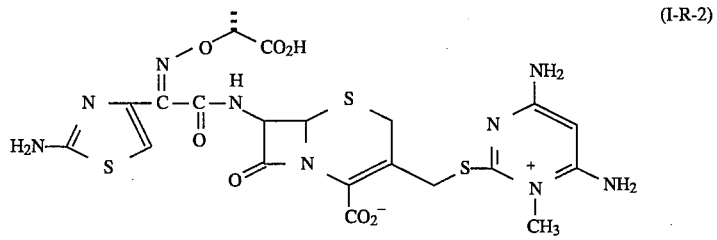
(I-R-2)

To a solution containing 500 mg of 3-acetoxymethyl-7-[(Z)- 2-(2-aminothiazol-4-yl)-2-[(R)-1-carboxyeth-1-oxy-imino]acetamido]- 3-cephem-4-carboxylic hydrochloride suspended In 5 ml of distilled water were added 200 mg of 4,6-diamino-1-methyl-2(1H)-pyrimidinethione and 800 mg of potassium iodide. The reaction solution was heated to 70° C., while the pH was adjusted to 7.1 to 7.2 with addition of aqueous sodium bicarbonate solution. The resultant solution was stirred for 4 hours, cooled to room temperature and adjusted to pH 3 to 3.5 with 2N-aqueous hydrochloric acid solution to produce precipitates which were washed with 5 ml of distilled water after filtration. The filter cake was applied to the,.chromatography on prep-column (ODS steel column, 19 mm×300 mm) using mixtures of ammonium phosphate buffer solution at pH 7 and acetonitrile (92:8) as an eluent, to give 195 mg of the title compound as a white solid (m.p.>182° C., dec.).

NMR: δ(D$_2$O, NaHCO$_3$, 270 MHz) 1.48(d, 3H), 3.53(s, 3H), 3.59(ABq, 2H), 4.36(ABq, 2H), 4.67(q, 1H), 5.17(d, 1H), 5.61(s, 1H), 5.73(d, 1H), 7.01(s, 1H).

MS: 610(FAB, M+1)

IR(KBr, cm$^{-1}$): 1775(β-lactam), 1635, 1535.

EXAMPLE 10

Synthesis of Compound (I-R-3)

This example shows how one of the isomeric compounds, 7-[(Z)-2-(2-aminothiazol-4-yl)-2-[(R)-1-carboxyeth-1-oxy-imino] acetamido]-3-[(4,6-diamino-1-ethylpyrimidinium-2-yl)thiomethyl]- 3-cephem-4-carboxylate, having the following formula (I-R-3), was synthesized:

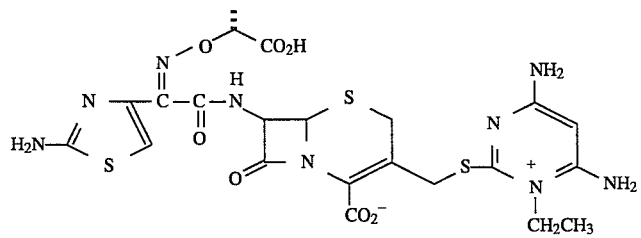
(I-R-3)

To a solution containing 500 mg of 3-acetoxymethyl-7-[(Z)- 2-(2-aminothiazol-4-yl)-2-[(R)-1-carboxyeth-1-oxy-imino]acetamido]- 3-cephem-4-carboxylic hydrochloride suspended In 5 ml of distilled water were added 200 mg of 4,6-diamono-1-ethyl-2(1H)-pyrimidinethione and 800 mg of potassium iodide. The reaction solution was heated to 70° C., while the pH was adjusted to 7.1 to 7.2 with addition of aqueous sodium bicarbonate solution. The resultant solution was stirred for 4 hours, cooled to room temperature and adjusted to pH 3 to 3.5 with 2N-aqueous hydrochloric acid solution to produce precipitates which were washed with 5 ml of distilled water after filtration. The filter cake was applied to the chromatography on prep-column (ODS steel column, 19 mm×300 mm) using mixtures of ammonium phosphate buffer solution at pH 7 and acetonitrile (92:8) as an eluent, to give 180 mg of the title compound as a white solid (m.p.>191° C., dec.).

NMR: δ(D$_2$O, NaHCO$_3$, 270 MHz) 1.34(t, 3H), 1.48(d, 3H), 3.59(ABq, 2H), 4.04(q, 2H), 4.34(ABq, 2H), 4.67(q, 1H), 5.15(d, 1H), 5.58(s, 1H), 5.71(d, 1H), 7.02(s, 1H).

MS: 624(FAB, M+1)

IR(KBr, cm$^{-1}$): 1775(β-lactam), 1640, 1530.

EXAMPLE 11

Synthesis of Compound (I-R-4)

This example shows how one of the isomeric compounds, 7-[(Z)-2-(2-aminothiazol-4-yl)-2-[(R)-1-carboxyeth-1-oxy-imino] acetamido]-3-[(4,6-diamino-1-propylpyrimidinium-2-yl)thiomethyl]- 3-cephem-4-carboxylate, having the following formula (I-R-4), was synthesized:

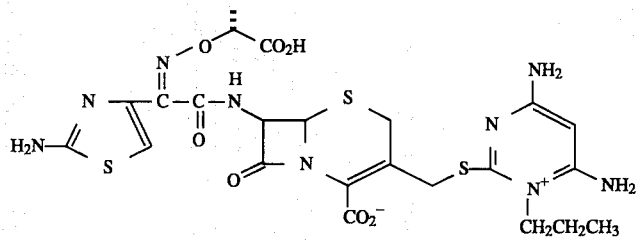

(I-R-4)

To a solution containing 500 mg of 3-acetoxymethyl-7-[(Z)- 2-(2-aminothiazol-4-yl)-2-[(R)-1-carboxyeth-1-oxyimino]acetamido]- 3-cephem-4-carboxylic hydrochloride suspended in 5 ml of distilled water were added 200 mg of 4,6-diamino-1-propyl-2(1H)-pyrimidinethione and 800 mg of potassium iodide. The reaction solution was heated to 70° C., while the pH was adjusted to 7.1 to 7.2 with addition of aqueous sodium bicarbonate solution. The resultant solution was stirred for 4 hours, cooled to room temperature and adjusted to pH 3 to 3.5 with 2N-aqueous hydrochloric acid solution to produce precipitates which were washed with 5 ml of distilled water after filtration. The filter cake was applied to the chromatography on prep-column (ODS steel column, 19 mm×300 mm) using mixtures of ammonium phosphate buffer solution at pH 7 and acetonitrile (90:10) as an eluent, to give 150 mg of the title compound as a white solid (m.p.>193° C., dec.).

NMR: δ($D_2O$, $NaHCO_3$, 270 MHz) 0.98(t, 3H), 1.48(q, 3H), 1.77(m, 2H), 3.61(ABq, 2H), 3.97(t, 2H), 4.38(ABq, 2H), 4.68(q, 1H), 5.19(d, 1H), 5.60(s, 1H), 5.73(s, 1H), 7.01(s, 1H).

MS: 638(FAB, M+1)

IR(KBr, $cm^{-1}$): 1778(β-lactam), 1645, 1525.

EXAMPLE 12

Synthesis of Compound (I-R-5)

This example shows how one of the isomeric compounds, 7-[(Z)-2-(2-aminothiazol-4-yl)-2-[(R)-1-carboxyeth-1-oxyimino] acetamido]-3-[(4,6-diamino-1'-phenylpyrimidinium-2-yl)thiomethyl]- 3-cephem-4-carboxylate, having the following formula (Z-R-5), was synthesized:

aqueous sodium bicarbonate solution. The resultant solution was stirred for 4 hours, cooled to room temperature and adjusted to pH 3 to 3.5 with 2N-aqueous hydrochloric acid solution to produce precipitates which were washed with 5 ml of distilled water after filtration. The filter cake was applied to the chromatography on prep-column (ODS steel column, 19 mm×300 mm) using mixtures of ammonium phosphate buffer solution at pH 7 and acetonitrile (87:13) as an eluent, to give 120 mg of the title compound as a white solid (m.p.>187° C., dec.).

NMR: δ($D_2O$, $NaHCO_3$, 270 MHz) 1.48(d, 3H), 3.48(ABq, 3H), 4.25(ABq, 2H), 4.67(q, 1H), 5.14(d, 1H), 5.69(s, 1H), 5.71(d, 1H), 7.00(d, 1H), 7.43–7.81(m, 5H).

MS: 672(FAB, M+1)

IR(KBr, $cm^{-1}$): 1777(β-lactam), 1650, 1515.

EXAMPLE 13

Synthesis of Compound (I-R-6)

This example shows how one of the isomeric compounds, 7-[(Z)-2-(2-aminothiazol-4-yl)-2-[(R)-1-carboxyeth-1-oxyimino] acetamido]-3-[(4,6-diamino-1,5-dimethylpyrimidinium-2-yl)thiomethyl] -3-cephem-4-carboxylate, having the following formula (I-R-6), was synthesized:

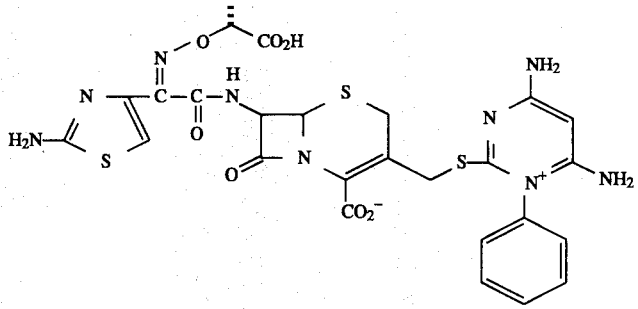

(I-R-5)

To a solution containing 500 mg of 3,acetoxymethyl-7-[(Z)- 2-(2-aminothiazol-4-yl)-2-[(R)-1-carboxyeth-1-oxyimino]acetamido]- 3-cephem-4-carboxylic hydrochloride suspended in 5 ml of distilled water were added 200 mg of 4,6-diamino-1-phenyl-2(1H)-pyrimidinethione and 800 mg of potassium iodide. The reaction solution was heated to 70° C., while the pH was adjusted to 7.1 to 7.2 with addition of

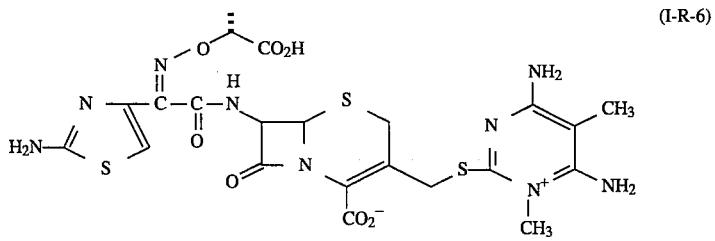

(I-R-6)

To a solution containing 500 mg of 3-acetoxymethyl-7-[(Z)- 2-(2-aminothiazol-4-yl)-2-[(R)-1-carboxyeth-1-oxy-imino]acetamido]- 3-cephem-4-carboxylic hydrochloride suspended in 5 ml of distilled water were added 200 mg of 4,6-diamino-1,5-dimethyl-2(1H)-pyrimidinethione and 800 mg of potassium iodide. The reaction solution was heated to 70° C., while the pH was adjusted to 7.1 to 7.2 with addition of aqueous sodium bicarbonate solution. The resultant solution was stirred for 4 hours, cooled to room temperature and adjusted to pH 3 to 3.5 with 2N-aqueous hydrochloric acid solution to produce precipitates which were washed with 5 ml of distilled water after filtration. The filter cake was applied to the chromatography on prep-column (ODS steel column, 19 mm×300 mm) using mixtures of ammonium phosphate buffer solution at pH 7 and acetonitrile (91:9) as an eluent, to give 210 mg of the title compound as a white solid(m.p.>179° C., dec.).

NMR: $\delta(D_2O, NaHCO_3, 270 \text{ MHz})$ 1.48(d, 3H), 1.92(s, 3H), 3.57(s, 3H), 3,60(ABq, 2H), 4.3a(ABq, 2H), 4.69(q, 1H), 5.17(d, 1H), 5.77(d, 1H), 7.03(s, 1H).

MS: 624(FAB, M+1)

IR(KBr, $cm^{-1}$): 1765(β-lactam), 1645, 1560.

EXAMPLE 14

Synthesis of Compound (I-R-7)

This example shows how one of the isomeric compounds, 7-[(Z)-2-(2-aminothiazol-4-yl)-2-[(R)-1-carboxyeth-1-oxy-imino] acetamido]-3-[(5-methyl-1,4,6-triaminopyrimi-dinium-2-yl)thiomethyl]- 3-cephem-4-carboxylate, having the following formula (I-R-7), was synthesized:

applied to the chromatography on prep-column (ODS steel column, 19 mm×300 mm) using mixtures of ammonium phosphate buffer solution at pH 7 and acetonitrile (93:7) as an eluent, to give 220 mg of the title compound as a white solid (m.p.>175° C., dec.).

NMR: $\delta(D_2O, NaHCO_3, 270 \text{ MHz})$ 1.48(d, 3H), 1.85(s, 3H), 3.58(ABq, 2H), 4.32(ABq, 2H), 4.67(q, 1H), 5.18(d, 1H), 5.71(d, 1H), 6.94(s, 1H).

MS: 625(FAB, M+1)

IR(KBr, $cm^{-1}$): 1770(β-lactam), 1635, 1565.

EXAMPLE 15

Synthesis and Isolation of Compounds (I-S-1) and (I-R-1) from a Mixture Thereof

As stated above, the S and R diastereomers can be obtained from a mixture thereof. Accordingly, this example is intended to show how their mixture was first synthesized; and then separated into the isomers having the structural formulas (I-S-1) and (I-R-1), respectively, as described in Examples 1 and 8 above.

To a solution containing 500 mg of 3-acetoxymethyl-7-[(Z)- 2-(2-aminothiazol-4-yl)-2-[(R, S)-1-carboxyeth-1-oxyimino]acetamido]- 3-cephem-4-carboxylic hydrochloride suspended in 5 ml of distilled water were added 200 mg of 1,4,6-triamino-2(1H)-pyrimidinethione and 800 mg of potassium iodide. The reaction solution was heated to 70° C., while the pH was adjusted to 7.1 to 7.2 with addition of aqueous sodium bicarbonate solution. The resultant solution was stirred for 4 hours, cooled to room temperature and

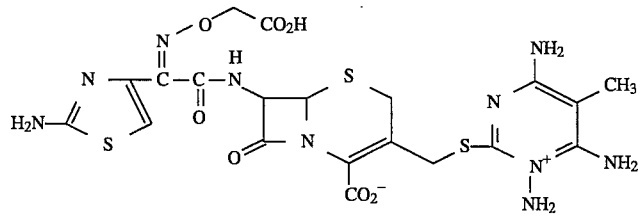

(I-R-7)

To a solution containing 500 mg of 3-acetoxymethyl-7-[(Z)- 2-(2-aminothiazol-4-yl)-2-[(R)-1-carboxyeth-1-oxy-imino]acetamido]- 3-cephem-4-carboxylic hydrochloride suspended in 5 ml of distilled water were added 200 mg of 5-methyl-1,4,6-triamino-2(1H)-pyrimidinethione and 800 mg of potassium iodide. The reaction solution was heated to 70° C., while the pH was adjusted to 7.1 to 7.2 with addition of aqueous sodium bicarbonate solution. The resultant solution was stirred for 4 hours, cooled to room temperature and adjusted to pH 3 to 3.5 with 2N-aqueous hydrochloric acid solution to produce precipitates which were washed with 5 ml of distilled water after filtration. The filter cake was adjusted to pH 3 to 3.5 with 2N-aqueous hydrochloric acid solution to produce precipitates which were washed with 5 ml of distilled water after filtration. The filter cake was applied to the chromatography on prep-column (ODS steel column, 19 mm×300 mm) using mixtures of ammonium phosphate buffer solution at pH 7 and acetonitrile (95:5) as an eluent, to give 90 mg and 80 mg of the title Compounds (I-S-1) and (I-R-1), respectively, as white solids.

The compounds synthesized in Examples 1 to 14 above are listed in Table 1 in a summary fashion. $R^1$ and $R^2$ shown in Table 1 have the same meanings as those of formula (I).

TABLE 1

Summary of Compounds Synthesized in Examples 1–14

| Compound | $R^1$ | $R^2$ |
|---|---|---|
| I-S-1 | $NH_2$ | H |
| I-S-2 | $CH_3$ | H |
| I-S-3 | $CH_2CH_3$ | H |
| I-S-4 | $CH_2CH_2CH_3$ | H |
| I-S-5 | phenyl | H |
| I-S-6 | $CH_3$ | $CH_3$ |
| I-S-7 | $NH_2$ | $CH_3$ |
| I-R-1 | $NH_2$ | H |
| I-R-2 | $CH_3$ | H |
| I-R-3 | $CH_2CH_3$ | H |
| I-R-4 | $CH_2CH_2CH_3$ | H |
| I-R-5 | phenyl | H |
| I-R-6 | $CH_3$ | $CH_3$ |
| I-R-7 | $NH_2$ | $CH_3$ |

The cephalosporin compounds (I) of the present invention, their non-toxic salts, esters, solvates and hydrates, as mentioned above, show potent antibacterial activities against a variety of general pathogenic microbial organisms including Gram-negative and Gram-positive bacteria; and, therefore, they are especially useful in therapy for treatment of bacterial infections in human beings and animals.

In order to illustrate their surprisingly superior antibacterial effectiveness, the minimal inhibitory concentrations (NIC) of the 14 compounds synthesized in Example 1 through 14 against standard strains were determined and compared with Ceftazidime of formula (C), which was used as the control compound. These NIC values were taken by employing a two-fold dilution method: that is, two-fold serial dilutions of each of the test compounds were made and dispersed in a Muller-Hinton agar medium; 2 μl of the standard test strain which had the $10^7$ CFU (Colony Forming Unit) per ml was inoculated on the medium; and these were incubated at 37° C. for 20 hours. The results of the NIC tests are shown in Table 2.

In addition, the acute toxicity tests for the 14 compounds were carried out at $LD_{50}$ by Intravenously administering each of the test compounds in varied amounts in a stepwise manner into 5 ICR mice (5 weeks old), which were observed for 14 days. The results are shown in the last row of Table 2.

As can be seen from Table 2, the diastereomers of the present invention, particularly those S isomers, exhibit surprisingly effective antibacterial activity against a broad spectrum of strains.

TABLE 2

Antibacterial Activity and Toxicity Data

| Strain | | MIC, μg/ml | | | | | | |
|---|---|---|---|---|---|---|---|---|
| | | I-S-1 | I-S-2 | 1-S-3 | I-S-4 | 1-S-5 | I-S-6 | I-S-7 |
| Bacillus cereus | ATCC 11778 | 32 | 32 | 32 | 32 | 32 | 64 | 84 |
| Bacillus megaterium | ATCC 9885 | 0.13 | 0.25 | 0.25 | 0.5 | 0.25 | 0.25 | 26 |
| Micrococcus luteus | ATCC 9341 | 0.25 | 0.13 | 0.25 | 0.13 | 0.25 | 0.25 | 0.25 |
| Staphylococcus aureus | ATCC 6638p | 4 | 2 | 2 | 2 | 4 | 4 | 4 |
| Staphylococcus epidermidis | ATCC 10537 | 2 | 1 | 1 | 1 | 4 | 2 | 2 |
| Staphylococcus fascalis | ATCC 12228 | 2 | 1 | 1 | 1 | 2 | 1 | 1 |
| Streptococcus faecalis | ATCC 29212 | >128 | >128 | >128 | >128 | >128 | >128 | >128 |
| Acinetobacter calcoaceticus | ATCC 15473 | 2 | 2 | 4 | 4 | 16 | 4 | 2 |
| Citrobacter freundii | ATCC 8090 | 0.031 | 0.016 | 0.031 | 0.031 | 0.13 | 0.016 | 0.016 |
| Enterobacter aerogenes | ATCC 29751 | 0.5 | 0.5 | 1 | 1 | 2 | 0.5 | 0.15 |
| Enterobacter cloacae | ATCC 27508 | 0.016 | <=0.008 | <=0.008 | <=0.008 | 0.031 | <=0.008 | <=0.008 |
| Escherichia coli | ATCC 10536 | 0.031 | 0.031 | 0.031 | 0.031 | 0.25 | 0.031 | 0.031 |
| Escherichia coli | ATCC 25922 | 0.031 | 0.016 | 0.031 | 0.031 | 0.25 | 0.031 | 0.016 |
| Klebsiella pneumoniae | ATCC 10031 | 0.031 | 0.016 | 0.031 | 0.031 | 0.13 | 0.031 | 0.016 |
| Morganella morganii | ATCC 8076h | <=0.008 | <=0.0.08 | <=0.008 | <=0.008 | <=0.008 | <=0.008 | <=0.QOB |
| Proteus mirabilis | ATCC 25933 | 0.016 | 0.016 | 0.031 | 0.031 | 0.13 | 0.031 | 0.016 |
| Proteus vulgaris | ATCC 6059 | 0.016 | 0.016 | 0.031 | 0.031 | 0.063 | 0.031 | 0.016 |
| Providencia rettgeri | ATCC 9250 | <=0.008 | <=0.008 | <=0.008 | <=0.008 | <=0.008 | <=0.008 | <=0.008 |
| Salmonella typhimurium | ATCC 14028 | 0.063 | 0.13 | 0.13 | 0.13 | 0.5 | 0.13 | 0.063 |
| Serratia marcescens | ATCC 27117 | 0.031 | 0.031 | 0.063 | 0.13 | 0.5 | 0.13 | 0.063 |
| Shigella flexneri | ATCC 11836 | 0.016 | <=0.008 | 0.016 | 0.031 | 0.13 | 0.016 | 0.016 |
| Shigella sonnei | ATCC 11060 | 0.031 | 0.031 | 0.063 | 0.063 | 0.25 | 0.031 | 0.031 |
| Pseudomonas aeruginosa | ATCC 25619 | 0.5 | 1 | 1 | 1 | 2 | 1 | 0.5 |
| Pseudomonas aerugionsa | ATCC 27853 | 0.5 | 0.5 | 1 | 1 | 4 | 1 | 0.5 |
| Pseudomonas aerugionsa | ATCC 10145 | 1 | 1 | 2 | 2 | 8 | 2 | 1 |
| $LD_{50}$ (g/kg mice, iv) | | >5 | >3 | >3 | >3 | >2 | >3 | >5 |

| Strain | | MIC, μg/ml | | | | | | |
|---|---|---|---|---|---|---|---|---|
| | | I-R-1 | I-R-2 | I-R-3 | I-R-4 | I-R-5 | I-R-6 | X-R-7 | CTZ* |
| Bacillus cereus | ATCC 11778 | 128 | >128 | 128 | 64 | 64 | 128 | 128 | 128 |
| Bacillus megaterium | ATCC 9885 | 0.5 | 1 | 1 | 0.5 | 0.5 | — | 0.5 | 0.25 |
| Micrococcus luteus | ATCC 9341 | 1 | 0.5 | 0.25 | 0.5 | 0.25 | 0.5 | 0.5 | 0.5 |
| Staphylococcus aureus | ATCC 6638p | 8 | 4 | 2 | 2 | 4 | 4 | 4 | 16 |
| Staphylococcus epidermidis | ATCC 10537 | 4 | 2 | 2 | 2 | 2 | 2 | 2 | 8 |
| Staphylococcus faecalis | ATCC 12228 | 2 | 2 | 1 | 1 | 2 | 2 | 2 | 4 |
| Streptococcus faecalis | ATCC 29212 | >128 | >128 | >128 | >128 | >128 | >128 | >128 | >128 |
| Acinetobacter calcoaceticus | ATCC 15473 | 2 | 4 | 4 | 8 | 16 | 4 | 4 | 4 |
| Citrobacter freundii | ATCC 8090 | 0.031 | 0.063 | 0.063 | 0.063 | 0.13 | 0.063 | 0.13 | 0.13 |
| Enterobacter aerogenes | ATCC 29751 | 0.5 | 1 | 0.5 | 1 | 1 | 1 | 2 | 4 |
| Enterobacter cloacae | ATCC 27508 | 0.016 | 0.016 | 0.016 | 0.016 | 0.031 | 0.016 | 0.063 | 0.031 |

TABLE 2-continued

| Antibacterial Activity and Toxicity Data | | | | | | | | | |
|---|---|---|---|---|---|---|---|---|---|
| Escherichia coli | ATCC 10536 | 0.031 | 0.063 | 0.063 | 0.063 | 0.13 | 0.063 | 0.063 | 0.13 |
| Escherichia coli . | ATCC 25922 | 0.031 | 0.031 | 0.063 | 0.063 | 0.25 | 0.13 | 0.063 | 0.13 |
| Klebsiella pneumoniae | ATCC 10031 | 0.031 | 0.031 | 0.031 | 0.063 | 0.063 | 0.063 | 0.063 | 0.063 |
| Morganella morganii | ATCC 8076h | <=0.008 | <=0.008 | <=0.008 | <=0.008 | <=0.008 | <=0.008 | <=0.008 | <=0.008 |
| Proteus mirabilis | ATCC 25933 | 0.031 | 0.031 | 0.031 | 0.063 | 0.063 | 0.031 | 0.031 | 0.063 |
| Proteus vulgaris | ATCC 6059 | 0.031 | 0.031 | 0.031 | 0.063 | 0.063 | 0.063 | 0.063 | 0.063 |
| Providencia rettgeri | ATCC 9250 | <=0.008 | <=0.008 | <=0.008 | <=0.008 | <=0.008 | <=0.008 | <=0.008 | <=0.008 |
| Salmonella typhimurium | ATCC 14028 | 0.063 | 0.13 | 0.13 | 0.25 | 0.5 | 0.13 | 0.25 | 0.25 |
| Serratia marcescens | ATCC 27117 | 0.031 | 0.063 | 0.063 | 0.13 | 0.5 | 0.13 | 0.13 | 0.25 |
| Shigella flexneri | ATCC 11836 | <=0.008 | 0.031 | 0.031 | 0.031 | 0.063 | 0.031 | 0.031 | 0.063 |
| Shigella sonnei | ATCC 11060 | 0.016 | 0.031 | 0.031 | 0.063 | 0.25 | 0.063 | 0.063 | 0.13 |
| Pseudomonas aeruginosa | ATCC 25619 | 0.5 | 2 | 1 | 1 | 2 | 2 | 2 | 1 |
| Pseudomonas aerugionsa | ATCC 27853 | 1 | 1 | 1 | 2 | 4 | 2 | 2 | 1 |
| Pseudomonas aerugionsa | ATCC 10145 | 2 | 2 | 2 | 4 | 8 | 2 | 2 | 2 |
| $LD_{50}$ (g/kg mice, iv) | | >5 | >3 | >3 | >3 | >2 | >3 | >5 | — |

CTZ*: Ceftazidime

In addition to the in vitro tests described above, in vivo absorbency tests for the two selected compounds of formulas (I-S-1) and (I-R-1), along with Ceftadizime, were carried out by administering intravenously, in a dose of 20 mg/kg, each of these two compounds into SD rats (male) weighing 220 to 340 g; and drawing blood samples from the femoral vein of the rats every hour after administration, which were analyzed by employing the bio-assay or agar well method. About 10 to 15 rats were used for each of the compounds.

TABLE 3

In Vivo Absorbency Test Data (Plasma Concentration: Pharmacokinetic Parameter)

| | Sampling Time (min) | Compound | | |
|---|---|---|---|---|
| | | I-S-1 | I-R-1 | CTZ |
| Plasma Conc. (μg/ml) | 1 | 147.3 | 170.4 | 135 |
| | 2.5 | 101.6 | 101.6 | 94 |
| | 5 | 72.6 | 76.9 | 71 |
| | 10 | 57.3 | 57.0 | 50 |
| | 20 | 37.0 | 39.1 | 26 |
| | 40 | 19.6 | 17.7 | 10 |
| | 60 | 11.2 | 10.1 | 4.7 |
| | 120 | 3.1 | 2.5 | 1.6 |
| | 180 | 1.5 | 0.7 | — |
| Parameter | T½(α) (min) | 7.6 | 4.7 | 5 |
| | T½(β) (min) | 37.5 | 30 | 20 |
| | ACU (μg.min/ml) | 2861 | 2750 | 1683 |
| | Urinary recovery (%) | 93 | 91 | — |

Notes: (1) Two-Compartment Model (2) Dose: 20 mg/kg (3) Tested Animal: Rats(male; 220–340 g)

From the data shown in Tables 2 and 3, it can be readily appreciated that the novel compounds of the present invention, especially those S isomers, possess surprisingly superior antibacterial potency of wide spectrum and excellent absorbency/pharmacokinetic characteristics.

We claim:

1. A cephalosporin compound represented by formula (I-S)

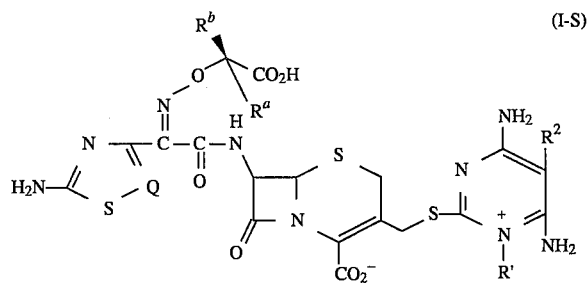

and the pharmaceutically acceptable non-toxic salts, physiologically hydrolyzable esters, hydrates and solvates thereof, wherein:

$R^1$ is a $C_{1-4}$ alkyl, $C_{3-4}$ alkenyl, $C_{3-4}$ cycloalkyl, amino optionally substituted with a $C_{1-4}$ alkyl radical, phenyl, or 2-, 4- or 6- substituted phenyl group with two or fewer substituents chosen from $C_{1-4}$ alkyl, $C_{1-3}$ alkoxy, halogen and hydroxy radicals;

$R^2$ is hydrogen or a $C_{1-4}$ alkyl group;

$R^a$ and $R^b$, which should be different from each other, are hydrogen or a $C_{1-4}$ alkyl group; and Q is N or CH.

2. The cephalosporin compound of claim 1 and the pharmaceutically acceptable non-toxic salts, physiologically hydrolyzable esters, hydrates and solvates thereof, wherein $R^1$ is a $C_{1-4}$ alkyl, $C_{3-4}$ alkenyl or amino group; $R^2$ is hydrogen or a $C_{1-2}$ alkyl group; $R^a$ and $R^b$, which should be different from each other, are hydrogen or a $C_{1-2}$ alkyl group; and Q is CH.

3. The cephalosporin compound of claim 1 and the pharmaceutically acceptable non-toxic salts, physiologically hydrolyzable esters, hydrates and solvates thereof, wherein $R^1$ is methyl, ethyl or amino group; $R^2$ is hydrogen or methyl; $R^a$ and $R^b$, which should be different from each other, are hydrogen or methyl; and Q is CH.

4. The cephalosporin compound of claim 1 and the pharmaceutically acceptable non-toxic salts, physiologically hydrolyzable esters, hydrates and solvates thereof, wherein the compound is 7-[ (Z)-2-(2-aminothiazol-4-yl)-2-[(S)-1-carboxyeth-1-oxyimino]acetamido- 3-[(1,4,6-triaminopyrimidinium-2-yl)thiomethyl]-3-cephem-4-carboxylate.

5. The cephalosporin compound of claim 1 and the pharmaceutically acceptable non-toxic salts, physiologically hydrolyzable esters, hydrates and solvates thereof, wherein the compound is 7-[ (Z)-2-(2-aminothiazol-4-yl)-2-[(S)-1- carboxyeth-1-oxyimino]acetamido- 3-[(4,6-diamino-1-methylpyrimidinium-2-yl)thiomethyl]-3-cephem- 4-carboxylate.

6. The cephalosporin compound of claim 1 and the pharmaceutically acceptable non-toxic salts, physiologically hydrolyzable esters, hydrates and solvates thereof, wherein the compound is 7-[(Z)-2-(2-aminothiazol-4-yl)-2-[(S)-1-carboxyeth-1-oxyimino]acetamido-3-[(4,6-diamino-1-ethylpyrimidinium- 2-yl)thiomethyl]-3-cephem-4-carboxylate.

7. The cephalosporin compound of claim 1 and the pharmaceutically acceptable non-toxic salts, physiologically hydrolyzable esters, hydrates and solvates thereof, wherein the compound is 7-[(Z)-2-(2-aminothiazol-4-yl)-2-[ (S)-1-carboxyeth- 1-oxyimino]acetamido-3-[(4,6-diamino-1-propylpyrimidinium-2-yl)thiomethyl]-3-cephem-4-carboxylate.

8. The cephalosporin compound of claim 1 and the pharmaceutically acceptable non-toxic salts, physiologically hydrolyzable esters, hydrates and solvates thereof, wherein the compound is 7-[(Z)-2-(2-aminothiazol-4-yl)-2-[(S)-1-carboxyeth- 1-oxyimino]acetamido-3-[(4,6-diamino-1-phenylpyrimidinium- 2-yl)thiomethyl]-3-cephem-4-carboxylate.

9. The cephalosporin compound of claim 1 and the pharmaceutically acceptable non-toxic salts, physiologically hydrolyzable esters, hydrates and solvates thereof, wherein the compound is 7-[(Z)-2-(2-aminothiazol-4-yl)-2-[(S)-1-carboxyeth- 1-oxyimino]acetamido-3-[(4,6-diamino-1,5-dimethylpyrimidinium- 2-yl)thiomethyl]-3-cephem-4-carboxylate.

10. The cephalosporin compound of claim 1 and the pharmaceutically acceptable non-toxic salts, physiologically hydrolyzable esters, hydrates and solvates thereof, wherein the compound is 7-[(Z)-2-(2-aminothiazol-4-yl)-2-[(S)-1-carboxyeth- 1-oxyimino]acetamido-3-[(5-methyl-1,4,6-triaminopyrimidinium- 2-yl)thiomethyl]-3-cephem-4-carboxylate.

11. A pharmaceutical composition comprising a therapeutically effective amount of a cephalosporin compound according to any one of claims 1 to 10.

* * * * *